(12) United States Patent
Milbourn et al.

(10) Patent No.: US 6,471,665 B1
(45) Date of Patent: Oct. 29, 2002

(54) POSTURAL DYNAMIC SPINAL EXTENSION BRACE AND METHOD

(75) Inventors: Jack R. Milbourn, Springfield, IL (US); James H. Campbell, Clarkston; Nicholas C. Zalinski, Madison Heights, both of MI (US)

(73) Assignee: Becker Orthopedic Appliance Company, Troy, MI (US)

( * ) Notice: Subject to any disclaimer, the term of this patent is extended or adjusted under 35 U.S.C. 154(b) by 0 days.

(21) Appl. No.: 09/569,726

(22) Filed: May 10, 2000

Related U.S. Application Data

(60) Provisional application No. 60/133,271, filed on May 10, 1999.

(51) Int. Cl.$^7$ .................................................. A61F 5/00
(52) U.S. Cl. ..................... 602/19; 128/103.1; 128/106.1
(58) Field of Search ............................... 602/5, 19, 32, 602/36, 60, 61; 128/95.1, 96.1, 99.1, 102.1–106.1, DIG. 19; 2/44

(56) References Cited

U.S. PATENT DOCUMENTS

| | | | |
|---|---|---|---|
| 2,582,930 A | * 1/1952 | Jewett | 128/78 |
| 3,094,984 A | * 6/1963 | Jewett | 128/78 |
| 3,095,875 A | * 7/1963 | Davidson et al. | 128/78 |
| 3,220,407 A | * 11/1965 | Connelly | 128/78 |
| 3,351,053 A | * 11/1967 | Stuttle | 128/78 |
| 3,548,817 A | * 12/1970 | Mittasch | 128/75 |
| 4,285,336 A | 8/1981 | Oebser et al. | 128/78 |
| 4,691,696 A | 9/1987 | Farfan de los Godos | 128/78 |
| 4,829,989 A | * 5/1989 | Deamer et al. | 128/78 |
| 5,176,622 A | * 1/1993 | Anderson et al. | 602/19 |
| 5,328,446 A | 7/1994 | Bunnell et al. | 602/16 |
| 5,503,621 A | * 4/1996 | Miller | 602/19 |
| 5,569,171 A | 10/1996 | Muncy | 602/5 |

* cited by examiner

*Primary Examiner*—Denise Pothier
(74) *Attorney, Agent, or Firm*—Ryndak & Suri

(57) ABSTRACT

A dynamic spinal extension brace is provided that comprises an upper frame having a sternum pad, a lower frame having a pubic pad, and a thoracic pad where the lower frame and upper frame can be positioned with respect to each other in more than a vertical dimension so as to accommodate even exaggerated curvatures of the thoracic spine. Also provided is a method of straightening and lifting the spine, using the inventive spinal brace.

28 Claims, 6 Drawing Sheets

POSTURAL DYNAMIC SPINAL EXTENSION BRACE AND METHOD

BACKGROUND OF THE INVENTION

This application claims the benefit of prior filed co-pending U.S. Provisional Application Serial No. 60/133,271, filed May 10, 1999, the disclosure of which is hereby expressly incorporated by reference.

FIELD OF THE INVENTION

This invention relates generally to a spinal brace that lifts and straightens the upper spine. More particularly, the present invention relates to a spinal brace that provides a spinal extension for the osteoporotic patient by directing a dynamic lifting and straightening force to the upper spine.

Spinal braces are applied to the spine of a human body to help restore or improve its function. Such braces generally rely upon the application of force to portions of the body other than the spine—e.g., the lower back, the upper back, the chest, or the abdomen, as examples—for asserting their corrective effect. Braces that lift and extend the thoracic spine may be useful for addressing conditions commonly associated with osteoporosis, such as shortening of stature, compression fractures of the spine, compression of the diaphragm, decreased lung capacity, and consistent or recurring pain.

Although a number of spinal braces are used today, such braces are generally "static" in nature, in that they have no "adjustable" components other than those permitting the lengthening and shortening of a vertical dimension. As a result, the utility of such braces may be limited by the degree of forward curvature, termed "kyphosis," that develops in the thoracic spine of the osteoporotic patient.

Accordingly, there exists a need for a dynamic spinal brace that can be adjusted in more than a vertical dimension so as to accommodate the complicated needs of osteoporotic patients including those patients having an exaggerated forward thoracic curvature.

SUMMARY OF THE INVENTION

In accordance with the present invention, there is provided a spinal brace for lifting and extending the upper spine. The spinal brace can be a dynamic device, providing a lifting and straightening force to the upper (thoracic) spine. In accordance with one aspect of the invention, an adjustable pivotal linkage system is provided between upper and lower pads or framework structures of the spinal extension brace. The upper framework pad or structure can be positioned to operatively interface with the chest wall regardless of the degree of kyphosis.

In accordance with the invention, the pivotal linkage can be located between the lower pad or framework structure and a side plate or similar structure of the inventive spinal brace. Alternatively, the pivotal linkage can be located between the upper pad or upper framework structure and a side plate or similar structure that connects (directly or indirectly) the upper and lower framework structures. Alternatively, the pivotal linkage may form an integral part of the side plate structure.

In accordance with another aspect of the invention, a spinal brace is provided that is composed of an upper anterior member adapted to be positioned over the sternum for applying a force against the chest wall, or lower anterior member adapted to be positioned over the person's lower abdomen or pelvic region, structure for pivotally connecting in a spaced orientation the lower anterior member with the upper anterior member. A thoracic support is provided that extends from the sides of the brace around the back of a person and may extend from one side of each of the lower and upper anterior members around the back of the person and back to the opposite side of the respective lower and upper members. Structure may also be provided for holding or retaining the lower anterior member against the pubic or pelvic region. The brace produces a force that tends to straighten the person's spine when worn in the operative position.

The structure for pivotally connecting the lower and upper anterior members in one embodiment may be a hinge member allowing for a rotational range of movement of the lower and upper anterior members in the direction of bending the person's spine forward (downward) and backward (upward or straightening). The hinge member may incorporate a one-way clutch to allow rotation in only one (upward) direction.

More particularly, in accordance with another aspect of the invention, the spinal brace comprises an upper anterior frame having a sternum pad for placement over the sternum, a lower anterior frame having an abdominal pad for placement over the pubic arch bone in the pubic or pelvic area, a thoracic pad for placement over the lower thoracic spine, and a left side plate and a right side plate for interfacing the upper anterior frame with the lower anterior frame.

In one embodiment, the upper anterior frame includes a laterally extending portion that is placed across the upper chest so the sternum pad aligns substantially with the sternum. The lateral portion extends laterally away from the sternum pad and terminates in an end on each side of the lateral portion. Preferably, such ends extend downwardly. The upper frame is fixedly secured to each of the side plates. The lower anterior frame comprises two connecting components separated by a lateral plate on which the abdominal pad is disposed. Each end of the lateral plate is pivotally attached to one of the connecting components, and the lower frame is further pivotally attached to the two side plates. Such pivotal attachments allow the lower and upper frames to be positioned as needed. The thoracic pad is secured to a flexible web that holds the pad in position when the web is fastened to the side plates. Also included in this embodiment is a structure for holding the lower anterior frame against the pubic or pelvic region of the patient's body. Such structure is preferably a flexible web, attachable to each of the side plates so that the web may be extended across the outer surface of the lower frame and tightened to cause the pubic pad to exert a posterior-directed force on the lower pubic area.

When the brace is affixed to the body of a person in a normal wear position, the brace is configured so that the upper frame becomes pivotally positioned to interface with the chest wall, the sternum pad is substantially positioned over the sternum, and each downwardly descending end of the upper frame substantially aligns with one side of the person's chest wall. The lateral plate of the lower anterior frame extends laterally across the lower abdomen and each of the connecting components preferably traverses upwardly around one side of the lower trunk of the person toward the corresponding downwardly descending end of the upper frame. The pubic pad is substantially positioned over the pubic arch bone in the pelvic area and is firmly held in place. The thoracic pad is substantially secured over the thoracic region of the back, and each side plate is substantially aligned with one side of the torso. When the brace is in position, the pubic pad exerts a posteriorly directed force upon the pelvic region, the sternum pad exerts a posteriorly directed force upon the chest area, and the thoracic pad exerts an opposing, anteriorly directed force on the thoracic back region. Preferably, the anterior force is between the two posterior forces. As a result of the opposing forces, all of which are directed substantially along a vertical axis of the body, the upper spine is dynamically lifted and straightened.

In another embodiment in accordance with invention, a spinal brace is provided for addressing the needs of an osteoporotic patient having an exaggerated thoracic curvature of the spine. The spinal brace comprises an upper anterior frame having a sternum pad, a lower anterior frame having an pubic pad, a thoracic pad, and two side plates—each of which is connected to the upper frame and the lower frame. As these elements have been described above, no further description is given here. This embodiment includes an abdominal flexible web that is extendable over the outer surface of the lower frame and can be tightened to cause the pubic pad to generate a force upon the pubic bone. Preferably, the abdominal web is securely affixed to an abdominal web fastener on one side plate and detachably affixed to a second abdominal web fastener on the opposite side plate.

When the brace of this embodiment is affixed to the body of an osteoporotic patient in a normal wear position, the brace is configured as described above. As a result of its configuration and correspondence with the patient's body, the brace exerts the three forces described above. These opposing forces dynamically lift and straighten the upper spine.

In yet another embodiment, a spinal brace is provided that creates a three-point pressure system for dynamically lifting and extending the thoracic spine of a person when affixed to the person's body. In this embodiment, the spinal brace includes the three pads, an upper chest frame, a lower torso frame, a flexible web secured to the thoracic pad, an abdominal web, and two side plates, as described above. In this embodiment, the brace further comprises a pivotal linkage system for pivotally attaching the lateral plate in the abdominal frame to each of the ascending bars therein and for pivotally attaching the lower torso frame to each side plate so that the upper frame can become pivotally positioned to interface with the chest wall. Such pivotal attachments allow the brace to be adjusted in more than a mere vertical dimension; that is, the upper frame can be positioned with respect to the lower frame in a way that optimizes the fit of the brace to the patient's body—such as when there is extreme thoracic curvature—and the extent to which the spine is lifted and extended.

When the brace of this embodiment is affixed to the body of a person in a normal wear position, it has substantially the same configuration as described above and substantially corresponds with the person's body, as described. As a result, a three-point pressure system is created and exerts the three forces, substantially as described above. Preferably, the anterior force is directed at a point of the body intermediate that of the two posterior forces. These opposing forces dynamically lift and straighten the upper spine.

Yet another embodiment in accordance with the invention is a spinal brace for lifting and straightening the spine of an osteoporotic patient, regardless of the degree of thoracic curvature. The spinal brace comprises an anterior composite and a thoracic support. The anterior composite includes an upper frame, a lower frame, and side plates where each side plate has a lumbar web fastener and an abdominal web fastener on its outer surface. The upper frame, lower frame, and side plates are as previously described, where the lower frame includes a lateral plate having two ends. Also included is a pivotal linkage, as described above. The thoracic support comprises a thoracic pad secured to a flexible web that is connectable to a web fastener on each side plate. When the brace of this embodiment is affixed to the patient's body, it has substantially the same configuration as described above. It also exerts substantially the same forces, resulting in the dynamic lifting and straightening of the upper spine, regardless of the degree of thoracic curvature.

Also provided, in accordance with the invention, is a method for lifting and straightening the spine of an osteoporotic patient regardless of the degree of thoracic curvature, using one of the spinal braces as described above. The method comprises holding the anterior composite, described above, against the front torso of the body; adjusting the position of the anterior composite so the sternum pad substantially aligns with the sternum and the pubic pad substantially aligns with the public arch bone; securing the back flexible web to position the thoracic pad over the thoracic region of the back so the thoracic pad exerts an anterior force upon the thoracic back; and securing the abdominal flexible web to position the pubic pad over the pubic arch bone. As a result of such securement, the lower portion of each side plate moves toward the lower frame and the upper frame is cantilevered backward so it becomes pivotally positioned to interface with the chest wall. This movement, in turn, causes the sternum pad and the pubic pad to each exert a posterior force upon their respective points of contact. As a result of the opposing forces, the upper spine is dynamically lifted and straightened.

One advantage of the present invention is the provision of a dynamic spine brace that may be adjusted in more than a vertical dimension. This is accomplished by a pivotal linkage system that provides a pivoting action at two points within the brace: (a) within the lower frame to allow the pubic pad to be pivotally positioned with respect to the upper frame; and (b) of the lower frame with respect to the side plates. As a result of the pivotal linkage, the lower and upper frames can be pivotally positioned with respect to each other so that the upper frame can interface with the chest wall regardless of the degree of kyphosis. The adjustment provided by the pivotal linkage system enables further reduction of the patient's thoracic curvature, as tolerated. Thus, by using the spinal brace in accordance with the invention, the patient may see an improvement in the conditions that are typically associated with osteoporosis, as described above.

Still other benefits and advantages of the invention will become apparent to those of ordinary skill in the art upon a reading and understanding of this specification.

DETAILED DESCRIPTION OF THE PREFERRED EMBODIMENT

Figure 1:
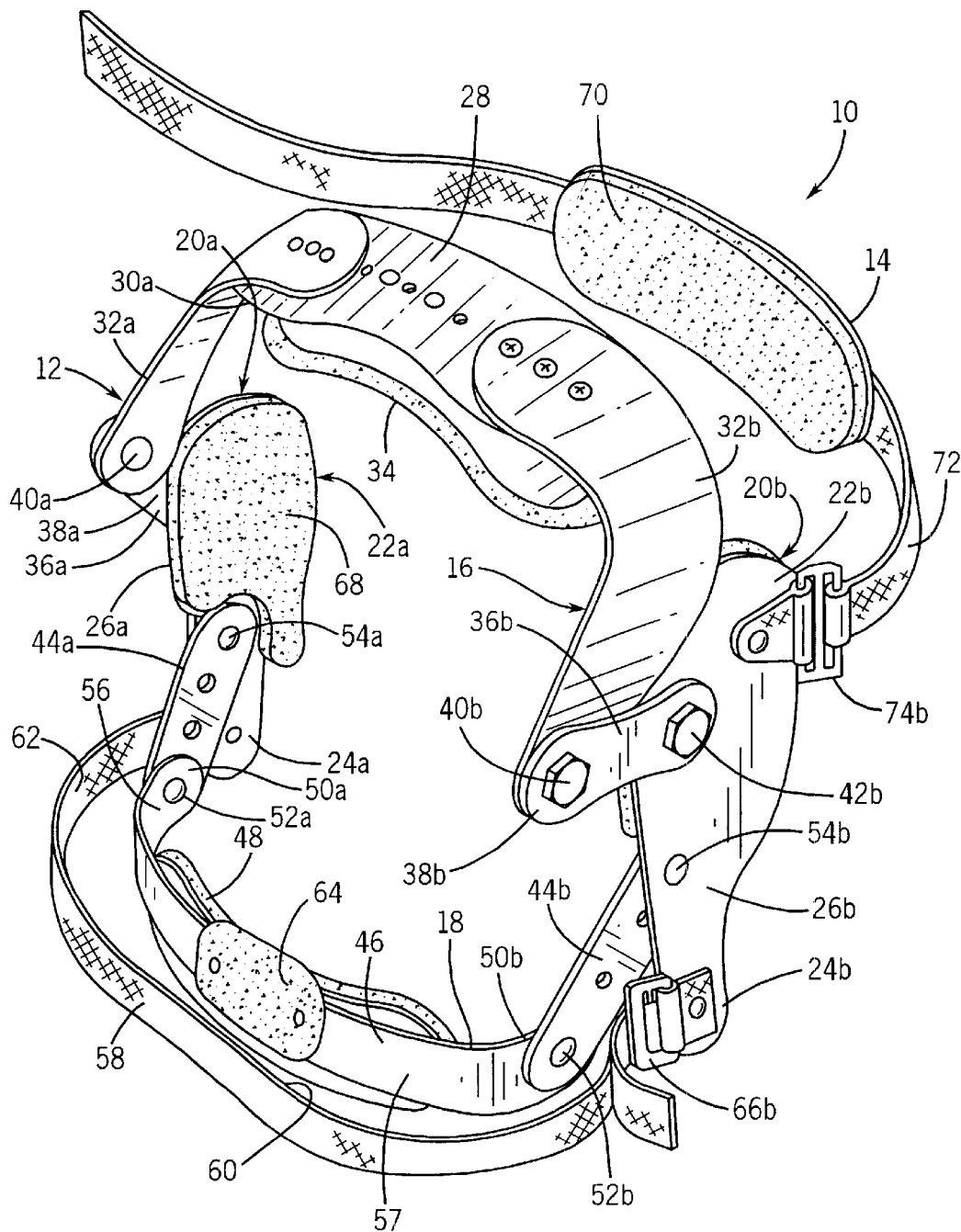
FIG. 1 is a perspective view of a spinal brace in accordance with the invention.
Figure 2:
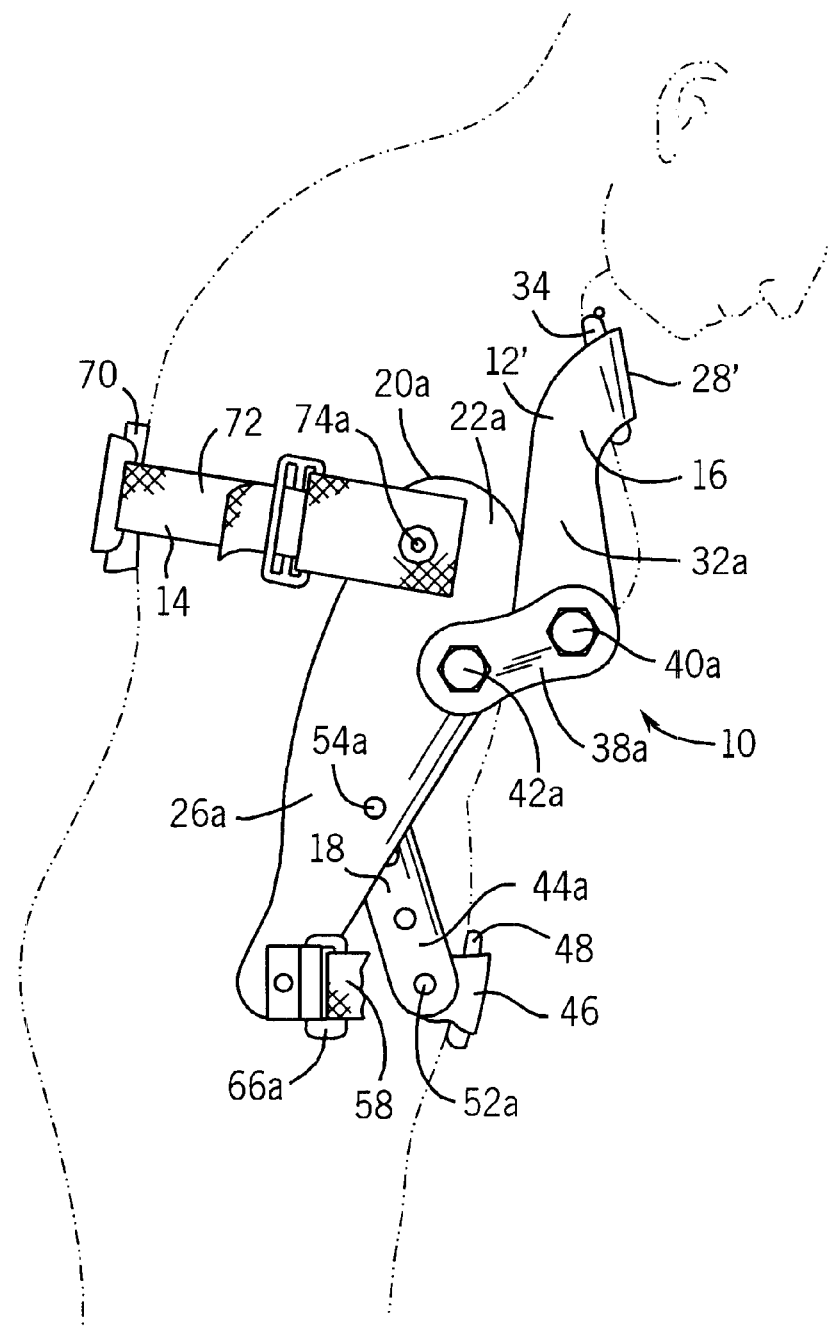
FIG. 2 is a side elevation view illustrating the spinal brace of FIG. 1 with minor variations as it is worn by an osteoporotic patient having a thoracic curvature.
Figure 3:
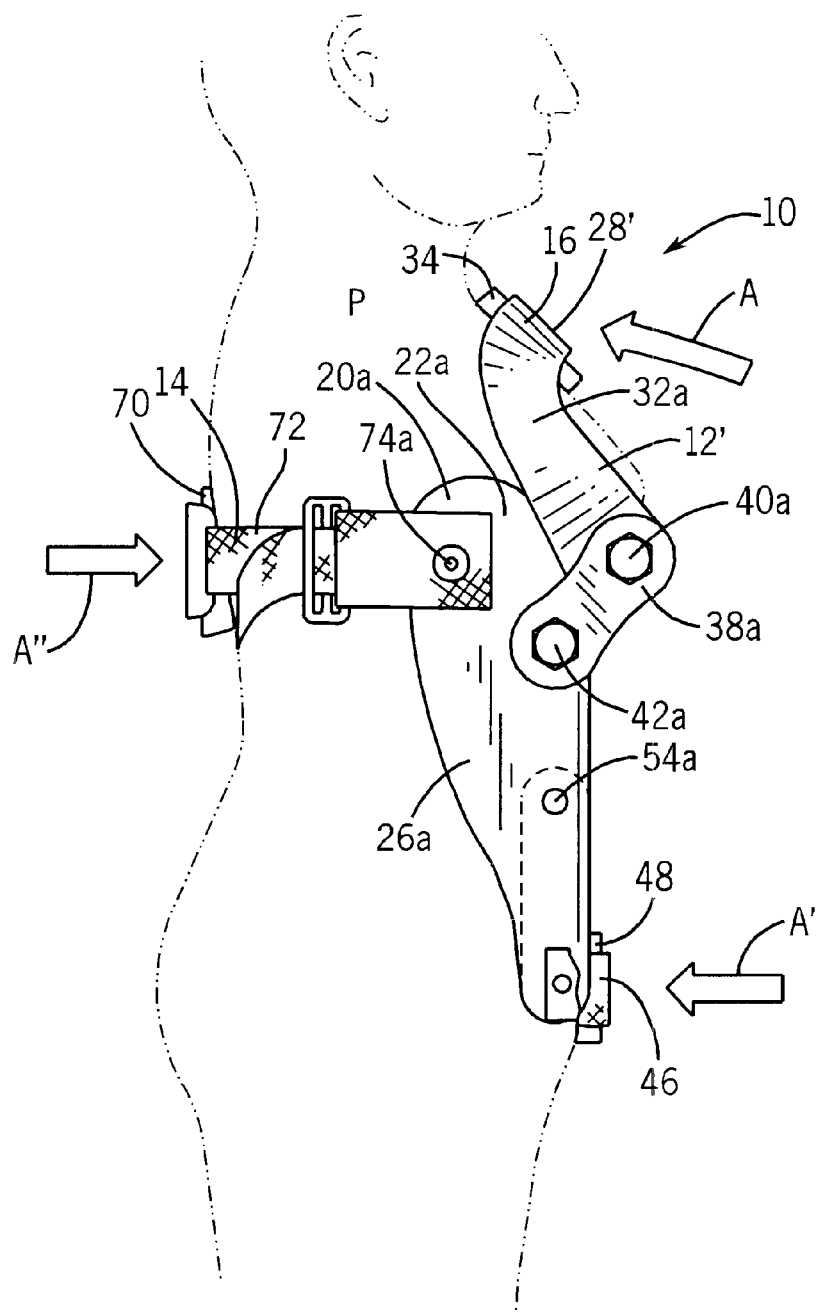
FIG. 3 is a side elevation view illustrating the spinal brace of FIG. 2 as it has helped achieve a lifting and extension of the thoracic spine of an osteoporotic patient.

Referring now to the drawings generally where like reference numerals denote like elements, the drawings are for purposes of illustrating preferred embodiments of the invention and not for purposes of limiting same, FIG. 1, for example, shows a spinal brace 10 which is used by osteoporotic patients as shown, for example, in FIGS. 2–3.

Shown in FIG. 1 is a perspective view of a spinal brace 10 in accordance with the invention for lifting and straightening the curved upper spine of a person. Spinal brace 10 comprises a rigid anterior composite structure 12 and a thoracic support 14. Anterior composite 12 comprises an upper anterior frame 16 and a lower anterior frame 18, where each is secured to side plates 20a,b of composite structure 12 as hereafter described.

On the anterior composite, each side plate 20a,b of anterior composite structure 12 serves to interface upper anterior frame 16 with lower anterior frame 18 and preferably aligns substantially with one side of the person's torso. Side plates 20a,b have upper portions 22a,b, lower portions 24a,b, and outer surfaces 26a,b.

As shown in FIG. 1, upper anterior frame 16 includes a sternum plate 28, typically having two opposing ends 30a,b, each of which is connected to a downwardly descending end 32a,b. A sternum pad 34 is disposed on and affixed to sternum plate 28 for placement against the sternum. Virtually any fastening structure may be used for affixing sternum pad 34 to sternum plate 28. Because such fastening and securement structures are well known in the art, a detailed disclosure of fasteners is not included herein. Sternum plate 28 is generally of a sufficient length and shape that it fits comfortably across the chest wall of person P. When the brace is affixed to the person's torso, downwardly descending ends 32a,b typically curve around the chest wall and descend downwardly to align substantially with the side of the chest wall. In an alternative embodiment, shown in FIGS. 2–3, upper frame 12' is one contiguous piece of a suitable shape and dimension for positioning against the person's body and includes a sternum plate 28' that extends into a downwardly descending portion 32a.

The shape of the upper frame can be generally as desired, as long as the sternum pad is provided as described herein. Typically, the shape of upper frame 16 corresponds to the curvature of the upper chest wall so as to facilitate positioning of the upper frame against the body.

A linkage structure 36a,b, which may be adjustable, provides secure attachments of upper frame 16 relative to the upper portions 22a,b of side plates 20a,b. Linkage structure 36 may be any structure that provides a linkage or bridge between upper frame 16 and side plates 20a,b. For example, in the embodiment illustrated in FIG. 1, linkage structure 36a,b may comprise a bridge member 38a,b that is firmly secured by at least one frame fastener 40a,b to one downwardly descending end 32a,b of upper frame 16 and by at least one side fastener 42a,b to side plate 20a,b where the securement precludes upper frame 16 from moving with respect to side plate 20a,b. Linkage structure 36 may be adjusted by loosening fasteners 40a,b and/or 42a,b to permit the orientation of sternum plate 28 relative to side plates 20a,b, and then tightening those fasteners when those elements are in the desired orientation. Alternatively, any other suitable linkage may be used to fixedly secure upper frame 16 from moving with respect to side plates 20a,b. Such linkage stabilizes upper frame 16 within anterior composite 12 so that when spinal brace 10 is affixed to the body, sternum pad 34 does not shift around the chest wall. In FIG. 1, bridge 38 is shown as a bar and fasteners 40, 42 are shown as bolts. Alternatively, bridge 38 may be any shape such as round, elliptical, octagonal, or hexagonal, for example, provided it immovably secures upper frame 16 to a side plate 20a,b. When necessary, bridge 38 can be loosened to allow upper frame 16 to be adjusted with respect to side plates 20a,b. Fasteners 40, 42 may be any suitable fastener that can be subsequently loosened for positionally adjusting upper frame 16 with respect to side plates 20a,b. As fasteners and bridging structures are well known in the art, no detailed disclosure is made herein. Alternatively, bridge members 38a,b could be utilized to provide a pivotal linkage in place of the pivotal linkage described with respect to lower anterior frame 18.

Lower anterior frame 18 comprises two connecting components or ascending bars or bridge members 44a,b, which are separated by a lateral plate 46 which cooperates with side plates 20a,b to provide a pivotal linkage. A pubic pad 48 is disposed on lateral plate 46 for placement substantially on the pubic arch bone. Lateral plate 46 has two ends 50a,b. A first pivotal connection 52a,b, disposed on each end 50a,b, attaches one end 50a,b to one ascending bar 44a,b. Via this connection, lateral plate 46 is afforded a range of rotational motion with respect to a horizontal axis drawn through pivotal linkage 52a,b. Typically, the rotational range of movement R is at least 180 degrees relative to a horizontal axis through ascending bars 44a,b. Preferably, however, the range of movement is 270 degrees, and most preferably 360 degrees.

A second pivotal linkage connection 54a,b is also associated with lower anterior frame 18. Second pivotal linkage connection 54a,b connects lower anterior frame 18 with side plates 20a,b. Second pivotal linkage connection 54a,b allows lower frame 18 to be pivoted about an axis running horizontally through pivotal linkage connection 54a,b so as to achieve an optimum positioning of the brace on the person's body and an optimum lifting and extension of the spine. As a result of pivotal linkage connection 54a,b, lower anterior frame 18 has a rotational range of motion of at least 180 degrees relative to side plates 20a,b through a horizontal axis running through such pivotal linkage system.

The pivotal linkage provided by pivotal linkage connections 52a,b and 54a,b may be provided by any suitable structure, including, for example, a rivet, bushing or other structure.

It is through the rotational range of movement afforded by pivotal linkage system 52a,b that when spinal brace 10 is affixed to the body of a person, sternum pad 34 and pubic pad 48 are pivotally adjusted with respect to each other to provide optimum lifting and fit, particularly for patients having exaggerated thoracic curvatures, and to provide extension of the spine.

As shown in FIGS. 1–3, lower frame 18 has an inner surface 56 and an outer surface 57. Pubic pad 48 is affixed to at least a portion of inner surface 56, and is generally disposed on lateral plate 46. When spinal brace 10 is affixed on a person's body in a normal wear condition, pubic pad 48 is positioned against the pubic arch bone where it is held in place so it exerts a posterior-directed force against the pubic bone. Typically, an abdominal flexible web 58 serves to hold pubic pad 48 in position so it does not shift on the body. Abdominal flexible web 58 is extendable over the outer surface of lower torso frame 18 and is typically detachably securable to at least a portion of lower torso frame 18. When tightened, abdominal web 58, which generally should be fastened to frame 18 to exert a force from both sides at the same time, holds pubic pad 48 in place so it can exert a posterior force upon the lower pelvic area.

The detachable securement of abdominal flexible web 58 to at least a portion of abdominal frame 18 results from the engagement of a fastening structure disposed on the abutting surfaces. Any suitable fastening structure may be used. One example of a suitable fastening structure includes a plurality of hooks 60 disposed on inner surface 62 of abdominal web 58 and a plurality of loops 64 disposed on a corresponding and complementary portion of outer surface 57 of lower frame 18 that lies in substantial horizontal alignment with the plurality of hooks 60.

Generally, abdominal flexible web 58 is secured to fasteners on both side plates 20a,b. Typically, when used for restricting the movement of pubic pad 48, abdominal flexible web 58 is secured to a first web fastener 66a, which is affixed to outer surface 26a of side plate 20a. Abdominal flexible web 58 then extends across the outer surface of lower anterior frame 18 to engage with a second web fastener 66b on outer surface 26b of the opposite side plate 20b. Preferably, as shown in FIGS. 1–2, web fasteners 66a,b are affixed to lower portion 24a,b of side plates 20a,b. Web fasteners 66a,b may be any suitable device for receiving a web of material and locking it in position; e.g., a frictional-locking clip. Because any suitable fasteners may find use in the spinal brace and fasteners are well known in the art, a detailed disclosure of these elements is not provided here.

Abdominal web 58 is typically made from any flexible webbing material. Such materials may be natural or synthetic, elastic or non-elastic, and include, for example, cotton, fabrics, nylon, polyester, plastic, acrylic, vinyl, leather and other suitable materials. Preferably, abdominal flexible web 58 is non-elastic in nature and may be any suitable width and length needed to secure pubic pad 48 in place. As abdominal flexible web 58 extends across lower frame 18, it is detachably secured to at least a portion of lateral plate 46.

Side plates 20a,b may have a side pad (not shown) affixed to the inner surface for comfort, as desired. Generally, the side pad, if present, will have a length as desired.

Sternum pad 34, abdominal pad 48, and thoracic pad 70 are dimensionally configured so that when spinal brace 10 is affixed in a normal wear position on the body and all three pads are secured in position, each pad 34, 48, and 70 disperses a force against an area of the body corresponding to its respective point of contact. Typically, pads 34, 48, and 70 may have a width of from about 1¾ inches to about 3½ inches and a length of from about 3 inches to about 14 inches. Generally, pads 34, 48, 70, and side pad 68 may have a thickness of from about ⅛ inch to about ¾ inches, primarily to provide a comfortable fit against the body. Pads 34, 48, 70, and 68 typically have a solid foam matrix-type composition. Any other suitable materials may, however, be used such as resinous compounds, fabrics, plastic, and others. In an alternative embodiment (not shown), pads 34, 48, 70, and 68 may comprise a liner of a suitable material filled with air or a gas, a fluid, a gel, or other flowable material including for example, silica beads or other flowable solids.

Thoracic support 14 comprises thoracic pad 70, which is secured to a flexible thoracic web 72. Thoracic pad 70 can be secured to thoracic web 72 by any suitable structure, such as adhesive, fasteners including a plurality of hooks in corresponding engagement with a plurality of loops, sewn stitches, or a looped structure for engaging a portion of the web, as examples. Because any suitable form of securement may be used and such forms of securement are well known in the art, a detailed disclosure is not provided here.

Thoracic web 72 is generally in the form of a flexible strap. Thoracic web 72 can be made from virtually any suitable material, natural or synthetic, elastic or non-elastic, including, for example, fabrics, polyester, plastic, acrylic, vinyl, leather and other suitable materials. Thoracic web 72 has any suitable width and length as needed for securing thoracic pad 70 firmly in place.

Thoracic web 72 is attachable to thoracic web fasteners 74a,b disposed on outer surface 26a,b of each side plate 20a,b. Thoracic web fasteners 74a,b are typically disposed on side plates 20a,b at a point laterally above thoracic web fasteners 66a,b. As a result, when spinal brace 10 is affixed to the patient's body, thoracic pad 70 is held in place over the thoracic region of the back and at a point laterally above thoracic flexible web 58.

Upper frame 16 and lower frame 18 may be made of any suitable material that, when affixed to the body, would allow sternum pad 34, thoracic pad 70, and pubic pad 48 to create a three-point pressure system for extending and straightening the spine. Examples of such materials include metals, fiberglass, plastic, resins, and flexible materials.

In accordance with the present invention, a method is provided for lifting and straightening the spine of an osteoporotic patient using the aforedescribed spinal brace. As spinal brace 10 has been described in detail above, further description is not provided here. The method comprises:

(1) positioning anterior composite 12 of upper frame 16, lower frame 18, and side plates 20a,b on the body;

(2) adjusting the position of upper frame 16 so sternum pad 34 substantially aligns with the sternum, each downwardly descending portion 32a,b substantially aligns with each side of the chest wall, pubic pad 48 substantially aligns with the pubic arch bone in the lower abdomen, and each upwardly ascending bar 44a,b substantially aligns with one side of the lower trunk;

(3) securing thoracic pad 70 so it aligns substantially with the thoracic region of the back; and (4) securing lower frame 18 in place so pubic pad 48 rests firmly in substantial alignment with the pubic arch bone and the inventive spinal brace is in the normal wearing position, such as shown with spinal brace 10 in FIGS. 2 and 3.

When brace 10 is in normal wearing position, lower portion 24a,b of side plates 20a,b moves toward lower frame 18 to exert a pressure on the pubic bone, and upper frame 16 is cantilevered backward to become pivotally positioned to interface with the chest wall. Such movement causes each of the three pads to exert a force against the patient's body in their respective area of contact. Sternum pad 34 and pubic pad 48 exert a posterior-directed force against the sternum and pubic arch bone, respectively in the direction of arrows A and A' in FIG. 3. Thoracic pad 70 exerts an opposing, anterior-directed force against the thoracic region of the back, with such force generally being directed in the direction of arrow A' at a point laterally between the two posterior-directed forces. All three forces are typically directed substantially along a vertical axis. As a result of the opposing forces, the upper spine is dynamically lifted and straightened, regardless of the degree of thoracic curvature.

FIGS. 2 and 3 show spinal brace 10 as it may be affixed to the body of an osteoporotic patient. FIG. 2 shows brace 10 as it is being used by a patient having a forward curvature of the thoracic spine; FIG. 3 shows the patient after having worn brace 10 to achieve a straightening and extension of the thoracic spine (assuming ideal conditions). In the embodiment shown in both figures, upper frame 12' is one contiguous piece of a suitable shape and dimension for positioning against the person's body and includes a lateral portion 28' that extends into a downwardly descending portion 32a. Downwardly descending portion 32a is fixedly secured to side plate 20a by linkage bar 38a and fasteners 40a and 42a. A pivotal linkage 54a attaches side plate 20a to connecting component 44a of lower frame 18 and pivotal linkage 52a attaches lateral plate 46 to connecting component 44a. Side plate 20a substantially aligns with the side torso of the patient. As shown in FIGS. 2–3, sternum pad 34 is positioned against the sternum. Pubic pad 48 is secured against the pubic bone, and thoracic pad 70 is held firmly in place against the thoracic region of the back. Thoracic pad 70 is secured to a lateral area of plate 20 above the fastener that holds pubic pad 48 in place. FIG. 2 shows abdominal web 58 cut away so as to not conceal the positioning of pubic pad 48.

Referring to FIGS. 4–8 there is illustrated another spinal brace 110 in accordance with the invention. Spinal brace 110 includes an upper anterior member 112, a lower anterior member 114, a hinge mechanism 116 and a thoracic support 116'.

Figure 4:
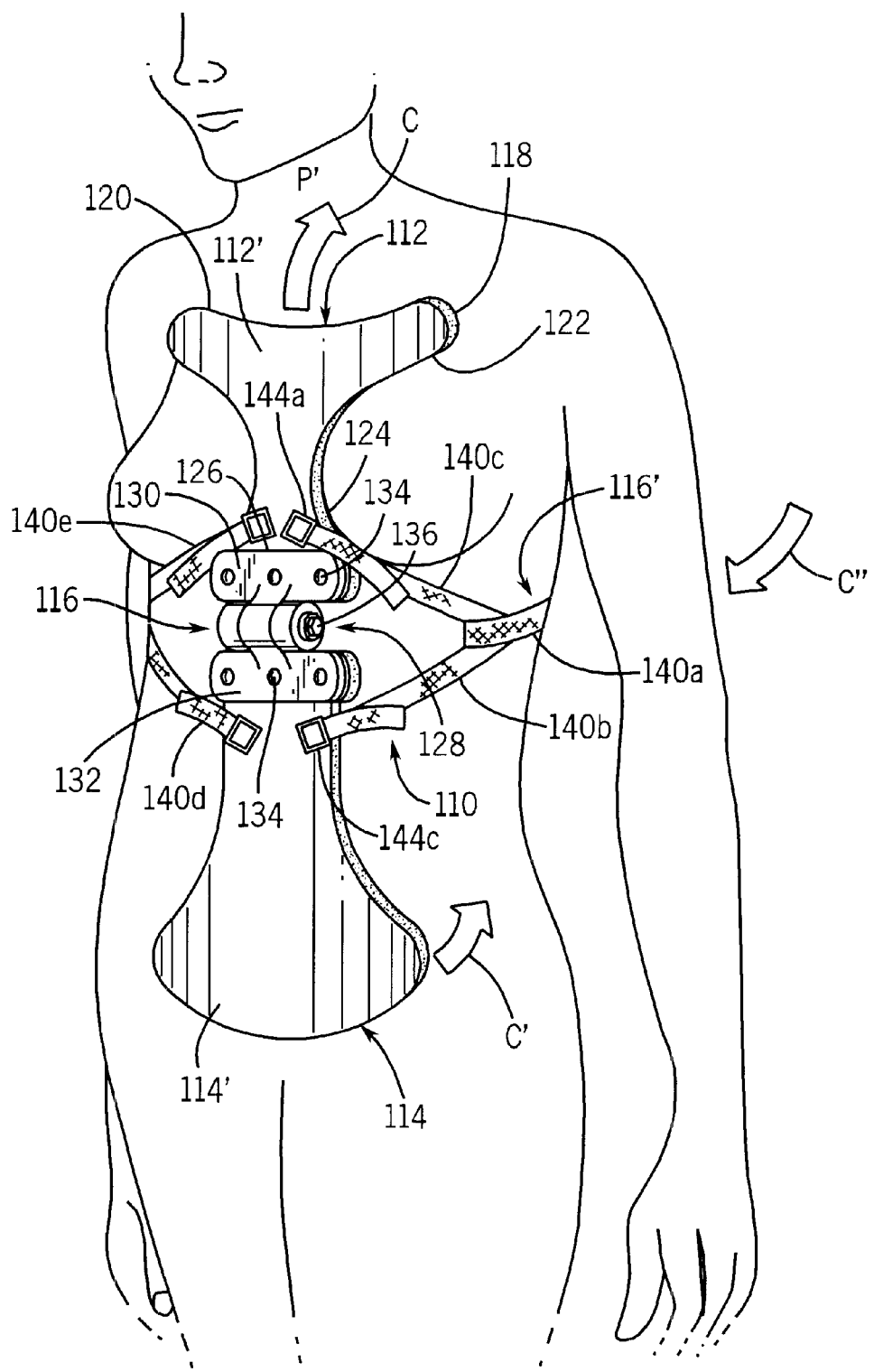
FIG. 4 is a perspective view of another embodiment of a spinal brace in accordance with the invention.

Upper anterior member 112 performs the same function as upper frame 12 and sternum plate 14 previously described and includes a pad 118 for comfortably contacting the sternum and upper chest of a person P' and applying a spine straightening and lifting force in the direction of arrow C on the upper chest and sternum. The forces applied by brace 110 are similar to those applied by brace 10 previously described. Member 112 is configured to comfortably fit over the upper chest of person P' as illustrated in FIG. 4, and has two laterally extending wings 120 and 122 and a downwardly extending wing 124 terminating in an attaching portion 126. The structural or outer portions 112' and 114' of members 112 and 114 can be constructed of a rigid material, such as metal, fiberglass or plastic, for example.

Lower anterior member 114 performs the same function as lower anterior frame 18 previously described and extends downwardly generally to the pubic or pelvic region or area of person P', and applies a force in the direction of arrow C' similar to the force of arrow A' previously described. Member 114 may also include a suitable pad 118' for comfortably contacting the pelvic or pubic area of person P'.

Hinge mechanism 116 includes a hinged joint 128 and upper and lower hinge flanges 130 and 132 to which the respective ends of upper and lower anterior members 112 and 114 are mounted by use of threaded fasteners 134 or other suitable fasteners as desired.

Hinged joint 128 can incorporate a one-way clutch mechanism so that the rotation or pivoting of hinged joint 128 is permitted only in one direction (in the direction of allowing the back or upper torso of person P' to be moved in an upward or spine straightening direction). One-way clutches are well known in the art and are described in detail in U.S. Pat. No. 5,328,446, issued Jul. 12, 1994 from U.S. Ser. No. 968,542, filed Oct. 29, 1992, the disclosure of which is hereby incorporated by reference. The one-way clutch may also have a "freewheeling mode" in which hinged joint 128 can pivot freely. In the one-way or treatment mode, hinged joint 128 allows (but does not urge) free movement in the spine straightening direction and movement in the opposite direction is prevented. The clutch can be of a type that allows movement in continuous or very small graduations and may be a sprague clutch, a ramp and roller clutch or a mechanical diode clutch. Alternatively, a ratchet-type mechanism could be employed. The clutch mode can be changed from freewheeling to one-way by the patient or the doctor, for example.

Figure 7:
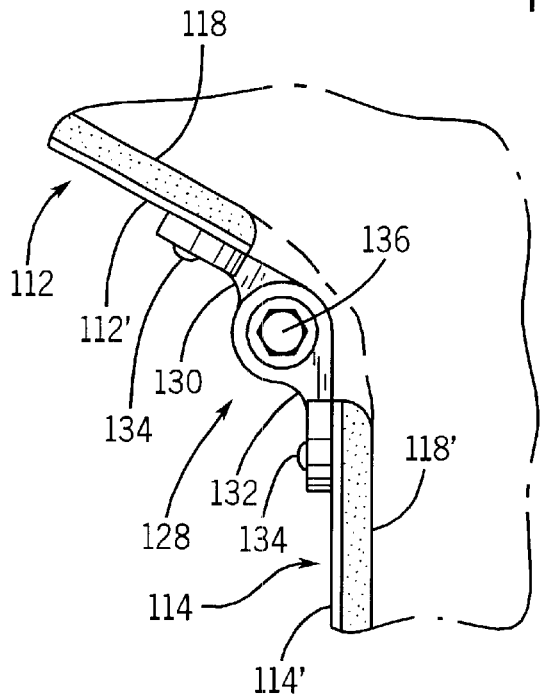
FIG. 7 is a fragmentary side elevation view of a portion of the spinal brace of FIG. 4.
Figure 8:
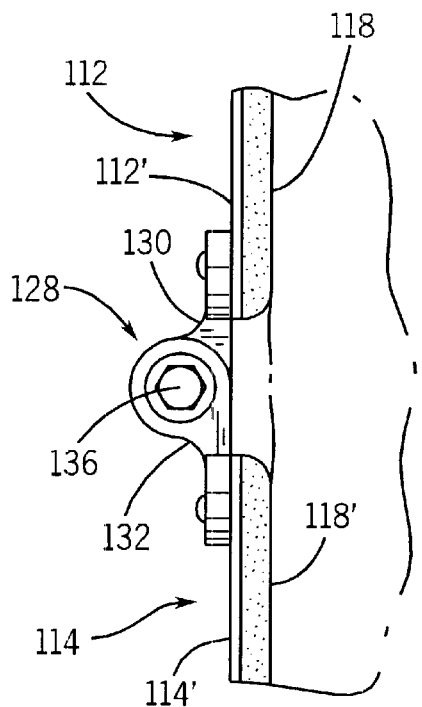
FIG. 8 is a fragmentary side elevation view of a portion of the spinal brace of FIG. 4.

Hinged joint 128 includes a pivot shaft 136 about which hinge mechanism 116 rotates. Hinge flanges 130 and 132 include suitable hinge bores to allow mounting to pivot shaft 136. As shown in FIGS. 7 and 8, the degree of rotation or pivoting can be substantial and may be in excess of 90° or 180° as desired.

Figure 5:
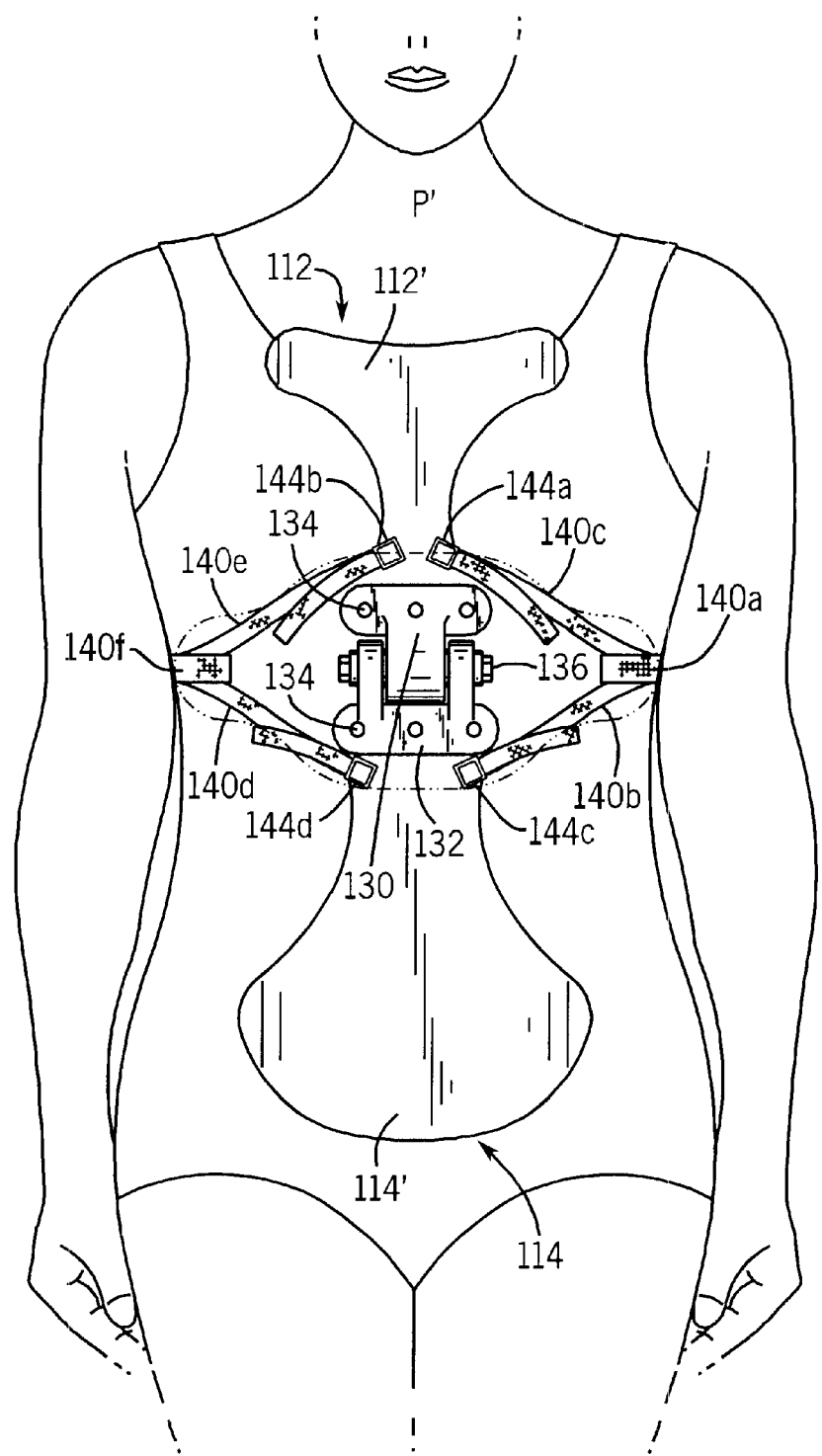
FIG. 5 is a front elevation view of the spinal brace of FIG. 4.
Figure 6:
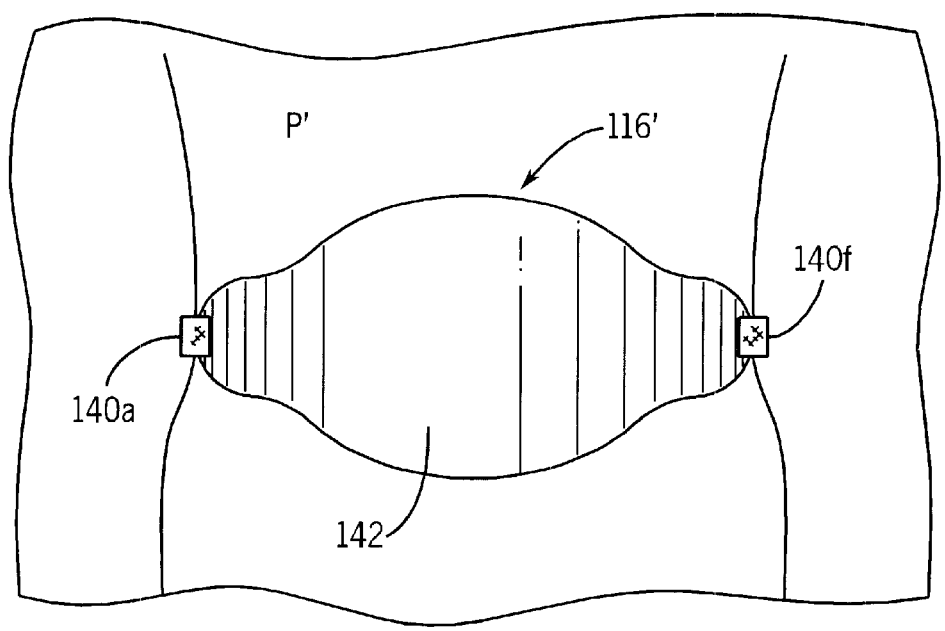
FIG. 6 is a rear elevation view of the spinal brace of FIG. 4.

Thoracic support 116' is composed of elastic strips or webs 140a–f that encircle person P' or the wearer as illustrated in FIGS. 4–6. A posterior pad 142 is located across the back of person P' and straps 140a and 140f are secured thereto. Buckles 144a–d are provided to permit adjustment of the tension of straps 140a–f to maintain brace 110 in the desired position and orientation on person P' and provide a force in the direction of arrow C", similar to the force described with respect to arrow A".

While the invention has been described with respect to certain preferred embodiments, as will be appreciated by those skilled in the art, it is to be understood that the invention is capable of numerous changes, modifications and alterations that are within the scope of the appended claims.

We claim:

1. A spinal brace for lifting and straightening the curved spine of an osteoporotic person, the person having a back, a chest wall, a sternum and a pelvic region and the brace having left and right sides, comprising:

an upper anterior member adapted to be positioned over the sternum for applying a force against the chest wall;

a lower anterior member adapted to be positioned in contact with and for applying a posteriorly directed force against the person's anterior pelvic region wherein said lower anterior member includes two interconnecting members separated by a laterally extending member that is pivotally connected to said two interconnecting members;

means for pivotally connecting in a spaced orientation the two interconnecting members with the upper anterior member;

a posterior thoracic support extending between the sides of the brace, said posterior thoracic support sized and configured to extend across at least a portion of the back of the person;

means for holding the lower anterior member against the pelvic region; and the brace producing a force that tends to straighten the person's spine when worn in an operative position.

2. The brace of claim 1 wherein the pivotal connecting means provides the lower anterior member with a rotational range of movement of at least 180 degrees relative to the upper anterior member.

3. The brace of claim 1 wherein the means for pivotally connecting comprises a side plate member secured to each respective end of said upper and lower members.

4. The brace of claim 3 wherein the means for holding the lower anterior member against the pelvic region comprises an abdominal webbing strap; said abdominal webbing strap being securable to the outer surface of one of the side plates and being engageable with a web fastener on the outer surface of the opposite side plate.

5. The brace of claim 1 wherein a side plate member extends between each end of said upper and lower members.

6. The brace of claim 5 wherein said upper anterior member is secured to the side plates by an intermediary member that restricts movement of said upper member with respect to each of said side plates.

7. The brace of claim 5 wherein the upper anterior member can be positionally adjusted with respect to the side plates to ensure that said upper member properly interfaces with the chest wall.

8. The brace of claim 1 further comprising two ends on said upper member wherein each of the two ends of the upper member are configured to align substantially with one side of the chest wall.

9. The brace of claim 1 wherein the means for pivotally connecting includes two pivotal joints at each end of said lower member.

10. A spinal extension brace for straightening the upper spine of an osteoporotic patient having a body with an exaggerated thoracic curvature of the spine, the patient further having a lower abdomen, a back, a chest area, a chest wall, a pelvic region, a pubic arch bone, a sternum and a thoracic region of the back, comprising:

two side plates, each side plate having an upper portion, a lower portion, an outer surface, a lumbar web fastener on the outer surface of each said plate, and an abdominal web fastener on the outer surface of each said plate;

a sternum pad disposed on an upper anterior frame; said upper anterior frame having a laterally extending portion terminating in two ends, said laterally extending portion for extending across the chest wall, each of said ends being fixedly secured to one of said side plates;

a pubic pad disposed on a lower abdominal frame, said lower abdominal frame having an outer surface and two interconnecting members separated by a lateral plate, said lateral plate being pivotally attached to each of said interconnecting members, said pubic pad being disposed on the lateral plate; said interconnecting members being pivotally attached to the lower portion of the side plates;

an abdominal flexible web for holding the lower frame against the pelvic region, said abdominal flexible web having an inner surface and an outer surfaces said abdominal flexible web being securely affixed to the abdominal web fastener on one of said side plates and being detachably securable to the abdominal web fastener on the opposite side plate; and a thoracic pad secured to a flexible strap, said flexible strap being detachably securable to the lumbar web fasteners on said side plates;

such that when the brace is affixed to the body of an osteoporotic patient in a normal wear position, the brace is configured so that the upper frame becomes pivotally positioned to interface with the chest wall, the sternum pad is substantially positioned over the sternum; the pubic pad is substantially positioned over and secured to the pubic arch bone in the pelvic region, the lateral plate of the lower frame extends laterally across the lower abdomen and each of the interconnecting members extends toward one end of the upper frame; the abdominal flexible web extends in substantial correspondence with the outer surface of the abdominal frame to be detachably secured to the abdominal web fastener on the opposite side plate; said abdominal flexible web further being detachably secured to at least a portion of the outer surface of the abdominal frame; and the thoracic pad is substantially secured over the thoracic region of the back;

such that the pubic pad exerts a posteriorly directed force upon the pelvic region, the sternum pad exerts a posteriorly directed force upon the chest area, and the thoracic pad exerts an opposing anteriorly directed force on the thoracic region of the back, wherein as a result of the opposing forces, the upper spine is dynamically lifted and straightened.

11. The brace of claim 10 wherein the lateral plate has a rotational range of movement of at least 180 degrees relative to the interconnecting members as a result of the pivotal attachment of the lateral plate to the interconnecting members so as to promote optimum positioning of the pubic pad on the pubic arch bone.

12. The brace of claim 10 wherein the interconnecting members in the abdominal frame have a rotational range of movement of at least 180 degrees relative to the side plates so as to allow the sternum pad and the pubic pad to be pivotally adjusted for optimum lifting and extension of the spine.

13. The brace of claim 10 wherein the pivotal attachment of the interconnecting members to the side plates is accomplished with a rivet.

14. The brace of claim 10 wherein the sternum pad, the pubic pad, and the thoracic pad are dimensionally configured to disperse pressure over a wide area of the body under the respective points of contact, each of said pads having a width of from about 1¾ inches to about 3½ inches and a length of from about 3 inches to about 14 inches.

15. The brace of claim 10, wherein the upper frame can be positionally adjusted with respect to the side plates to ensure that said upper frame properly interfaces with the chest wall.

16. The brace of claim 10 wherein the anteriorly directed force is exerted at a point, and within substantial vertical alignment with, the points where the two posteriorly directed forces are directed.

17. The brace of claim 10 further comprising a fastener for detachably securing at least a portion of the inner surface of the abdominal web to a corresponding and substantially aligned portion of the outer surface of the abdominal frame; one part of the fastener being disposed on the outer surface of the abdominal frame and a corresponding part of the fastener being disposed on the inner surface of the abdominal web, such that when the abdominal web is extended across the abdominal frame, each part of the fastener engages to detachably secure the abdominal web to the abdominal frame.

18. The brace of claim 10 wherein the abdominal flexible web comprises an inner surface and a plurality of hooks disposed on at least one portion of the inner surface, and wherein the abdominal frame comprises a plurality of loops disposed on a corresponding portion of the outer surface of the abdominal frame; such that when the abdominal web is extended across the abdominal frame, the plurality of loops engages the plurality of hooks to detachably secure the abdominal web to the abdominal frame.

19. The brace of claim 10 wherein the detachable securement of the abdominal flexible web to one of said side plates is via a friction locking loop affixed to said side plate.

20. A spinal brace for dynamically lifting and extending the thoracic spine of a person having a body with a thoracic region, a back, a pelvic region, a chest wall, a sternum, a pubic arch bone, a lower abdomen and a chest areas by creating a three-point pressure system when affixed to the patient's body, comprising:

two side plates;

a thoracic pad secured to a flexible web, said flexible web being connectable to said side plates for exerting an anterior force on the thoracic region;

a sternum pad disposed on an upper chest frame, said upper chest frame extending laterally across the chest wall and terminating in two downwardly descending ends, said upper chest frame being immovably secured to one of said side plates;

a pubic pad disposed on a lower anterior frame; said lower anterior frame having a lateral plate and two upwardly ascending bars, said lateral plate being pivotally attached to each of said ascending bars;

an abdominal flexible web for holding the lower anterior frame against the pelvic region, said abdominal flexible web being securely fastened to one of said side plates and being extendable across the outer surface of the lower anterior frame to detachably engage with a web fastener on the outer surface of the opposite side plate; and a pivotal linkage system for pivotally attaching the lateral plate of the lower anterior frame to each of said ascending bars and for pivotally attaching the lower anterior frame to each of said side plates so that said upper frame can become pivotally positioned to interface with the chest wall;

such that when the brace is affixed to the body of an osteoporotic patient in a normal wear position, the brace is configured so that the upper frame becomes pivotally positioned to interface with the chest wall, the sternum pad is substantially positioned over the sternum, the pubic pad is substantially positioned over the pubic arch bone in the pelvic region, the lateral plate of the lower anterior frame extends laterally across the lower abdomen and each of the upwardly ascending bars traverses upwardly toward the corresponding downwardly descending end of the upper frame; the abdominal flexible web firmly holds the abdominal pad in position against the pelvic region; and the thoracic pad is substantially secured over the thoracic region of the back;

so that the pubic pad exerts a first force upon the pelvic region, the sternum pad exerts a second force upon the chest area, and the thoracic pad exerts a third, opposing force upon the thoracic back region, creating a three-point pressure system which causes the upper spine to be dynamically lifted and straightened.

21. The brace of claim 20 wherein the upper chest frame further comprises a bridging member for attachment to the side plates so as to preclude movement of said upper frame with respect to either of said side plates.

22. The brace of claim 20 wherein the upper frame can be positionally adjusted with respect to the side plates to ensure that said upper frame properly interfaces with the chest wall.

23. A brace for lifting and straightening the upper spine of an osteoporotic patient regardless of the degree of thoracic curvature, the patient having a body including a sternum, a chest area, a chest wall, a pelvic region, a pubic arch bone, a lower abdomen, a thoracic region of the back, wherein the brace comprises:

an anterior composite and a thoracic support;

said anterior composite having an upper frame, a lower anterior frame, and opposing side plates; each said side plate having an outer surface, a lumbar web fastener on the outer surface, and an abdominal web fastener on the outer surface;

said upper frame having a lateral extension for extending laterally across the chest wall and having a sternum pad for placement on the sternum;

said lower frame comprising a lateral plate and two ascending bars, said lateral plate having two ends, each said end being pivotally attached to one of the ascending bars, and a pubic pad being disposed on the lateral plate; said lower frame being pivotally attached to each of said side plates;

an abdominal flexible web for holding the abdominal frame against the pelvic region, said abdominal flexible web being securely affixed to the abdominal web fastener on one of said side plates and detachably engageable with the abdominal web fastener on the opposite side plate; and a pivotal linkage for pivotally attaching the lateral plate of the lower frame to each of said ascending bars and for pivotally attaching the lower frame to each of said side plates so that said upper frame can become pivotally positioned to interface with the chest wall;

said thoracic support comprising a thoracic pad being secured to a flexible web, said flexible web being connectable to the lumbar web fastener on each of said side plates;

wherein when the spinal brace is affixed to the patient's body, the brace is configured so that the upper frame becomes pivotally positioned to interface with the chest wall, the sternum pad is substantially positioned over the sternum, a portion of the upper frame substantially aligns with one side of the person's chest wall; the pubic pad is substantially positioned over the pubic arch bone in the pelvic region and is substantially held in place; the lateral plate of the lower anterior frame extends laterally across the lower abdomen; and the thoracic pad is substantially secured over the thoracic region of the back;

such that the pubic pad exerts a posterior-directed force upon the pelvic region, the sternum pad exerts a posterior-directed force upon the chest area, and the thoracic pad exerts an anterior-directed force upon the thoracic region of the back, so that as a result of the forces, the upper spine of the osteoporotic patient is dynamically lifted and straightened, regardless of the degree of thoracic curvature.

24. A method for lifting and straightening the upper spine of an osteoporotic patient regardless of the degree of thoracic curvature using a spinal brace, the person having a body with a chest, a chest wall, a pubic arch bone, a thoracic region of the back, a front torso, a sternum and a spine including a thoracic spine, wherein the brace comprises:

an anterior composite having an upper frame, a lower abdominal frame, and two side plates;

said upper frame having a lateral extension and a sternum pad disposed thereon for positioning the upper frame on the chest wall, said upper frame being secured to each said side plate;

said lower frame comprising a lateral plate with two ends, each said end being pivotally attached to an ascending bar, and an abdominal pad being disposed on the lateral plate for positioning on the pubic arch bone, each said ascending bar being pivotally attached to one of said side plates;

an abdominal flexible web for holding the pubic pad in position over the pubic arch bone so said pubic pad exerts pressure on the patient's body, said flexible web being affixed to one said side plate and detachably securable to the outer surface of the lower frame and to the other said side plate;

a thoracic support comprising a thoracic pad for placement over the thoracic region of the back, said thoracic pad being secured to a thoracic flexible web connectable to each said side plate for exerting an anterior-directed force on the thoracic region of the back; and each said side plate further having a receiving member for securing the abdominal flexible web thereto and a receiving member for securing the thoracic flexible web thereto;

said method comprising;

placing the anterior composite on the front torso;

adjusting the position of the anterior composite so the sternum pad substantially aligns with the sternum and the pubic pad substantially aligns with the pubic arch bone;

securing the thoracic flexible web to position the thoracic pad over the thoracic region of the back so that said thoracic pad exerts an anterior pressure on the thoracic spine; and securing the abdominal flexible web to position the pubic pad over the pubic arch bone, such securement causing the lower portion of each side plate to move toward the abdominal frame and the upper frame to be cantilevered backward and pivotally positioned to interface with the chest wall, such movement further causing the sternum pad and the pubic pad to exert a posterior force on the chest and pelvic regions, respectively, so that as a result of said posterior forces and the opposing anterior-directed force, the upper spine is dynamically lifted and straightened.

25. The method of claim 24 wherein the forces are exerted such that the anterior-directed force upon the thoracic region of the back is intermediate that of the two posterior-directed forces.

26. The method of claim 24 wherein the step of securing the position of the pubic pad comprises attaching the abdominal flexible web to one of said side plates so said abdominal flexible web extends in correspondence over the abdominal frame and attaches to at least a portion of the abdominal frame.

27. A method of straightening and extending the spine of a person using a spinal brace, the person having a body including a sternum, a pelvic region, a lower pelvic area, a thoracic region of the back, a chest wall, a front torso, a pubic arch bone, a thoracic spine and a chest, wherein the brace comprises:

an anterior composite and a thoracic support;

said anterior composite having an upper frame, a lower abdominal frame, and side plates; each said side plate having a lumbar web fastener and an abdominal web fastener;

said upper frame for extending laterally across the chest wall and having a sternum pad for positioning on the sternum, said upper frame being securely attached to each of said side plates;

said lower frame for extending laterally across the lower abdomen and having a pubic pad for positioning on the lower pelvic area, said abdominal frame having two ascending bars separated by a lateral plate pivotally attached to said ascending bars;

an abdominal flexible web for holding the abdominal frame against the pelvic region so said pubic pad exerts a force against the pelvic region, said abdominal flexible web being affixed to the abdominal web fastener on one of said side plates and being extendable in substantial correspondence with the outer surface of the abdominal frame to be detachably secured to the opposite said side plate; said abdominal flexible web further being detachably secured to at least a portion of the abdominal frame;

said thoracic support comprising a thoracic pad for placement over the thoracic region of the back, said thoracic pad being held in place by a thoracic flexible web secured to the thoracic pad and to one of said side plates and being detachably fastened to the other side plate; and a pivotal linkage for pivotally attaching the lateral plate in the abdominal frame to each of the ascending bars therein and for pivotally attaching the abdominal frame to each of said side plates so that the upper frame can be pivotally positioned to interface with the chest wall;

said method comprising:

placing the anterior composite on the front torso;

adjusting the position of the anterior composite so the sternum pad substantially aligns with the sternum and the pubic pad substantially aligns with the pubic arch bone;

securing the thoracic flexible web to position the thoracic pad over the thoracic region of the back so that said thoracic pad exerts an anterior-directed force on the thoracic spine; and securing the abdominal flexible web to position the pubic pad over the pubic arc bone;

such securement causing the lower portion of each side plate to move toward the abdominal frame and the upper frame to be cantilevered backward and pivotally positioned to interface with the chest wall, such movement further causing the sternum pad and the pubic pad to exert a posterior force on the chest and pelvic regions, respectively, so that as a result of said posterior forces and the opposing anterior-directed force, the upper spine is dynamically lifted and straightened.

28. A spinal brace for lifting and straightening the curved spine of an osteoporotic person, the person having a back, a chest wall, a sternum and a pelvic region and the brace having left and right sides, comprising:

an upper anterior member adapted to be positioned over the sternum for applying a force against the chest wall;

a lower anterior member adapted to be positioned in contact with and for applying a posteriorly directed force against the person's anterior pelvic region, the lower anterior member having an outer surface;

means for pivotally connecting in a spaced orientation the lower anterior member with the upper anterior member;

a posterior thoracic support extending between the sides of the brace, said posterior thoracic support sized and configured to extend across at least a portion of the back of the person;

means for holding the lower anterior member against the pelvic region comprising an abdominal webbing strap; said abdominal webbing strap being detachably affixed to at least a portion of the outer surface of the lower anterior frame; and the brace producing a force that tends to straighten the person's spine when worn in an operative position.

* * * * *

UNITED STATES PATENT AND TRADEMARK OFFICE
CERTIFICATE OF CORRECTION

PATENT NO.    : 6,471,665 B1                                        Page 1 of 1
DATED         : October 29, 2002
INVENTOR(S)   : Jack R. Milbourn et al.

It is certified that error appears in the above-identified patent and that said Letters Patent is hereby corrected as shown below:

<u>Column 4,</u>
Line 33, delete "spine" and insert therefor -- spinal --.

<u>Column 8,</u>
Line 63, delete " A' " and insert therefor -- A" --.

<u>Column 11,</u>
Line 40, delete "surfaces" and insert therefor -- surface, --.

<u>Column 12,</u>
Line 59, delete "areas" and insert therefor -- area, --.

Signed and Sealed this

Twenty-fifth Day of March, 2003

JAMES E. ROGAN
*Director of the United States Patent and Trademark Office*